United States Patent
Pennemann et al.

(10) Patent No.: US 9,518,006 B2
(45) Date of Patent: Dec. 13, 2016

(54) METHOD FOR PRODUCING DIAMINOTOLUENE

(71) Applicant: Covestro Deutschland AG, Leverkusen (DE)

(72) Inventors: Bernd Pennemann, Bergisch Gladbach (DE); Amgad Salah Moussa, Cologne (DE); Bastian Mahr, Bergisch Gladbach (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/027,327

(22) PCT Filed: Oct. 2, 2014

(86) PCT No.: PCT/EP2014/071125
§ 371 (c)(1),
(2) Date: Apr. 5, 2016

(87) PCT Pub. No.: WO2015/052068
PCT Pub. Date: Apr. 16, 2015

(65) Prior Publication Data
US 2016/0244402 A1 Aug. 25, 2016

(30) Foreign Application Priority Data
Oct. 8, 2013 (EP) .................................. 13187648

(51) Int. Cl.
C07C 209/36 (2006.01)
(52) U.S. Cl.
CPC .................... C07C 209/36 (2013.01)

(58) Field of Classification Search
None
See application file for complete search history.

(56) References Cited

U.S. PATENT DOCUMENTS

| | | |
|---|---|---|
| 3,093,685 A | 6/1963 | Hort et al. |
| 3,136,818 A | 6/1964 | Sperber et al. |
| 3,636,152 A | 1/1972 | Szigeth |
| 4,740,621 A | 4/1988 | Adams et al. |
| 5,808,157 A | 9/1998 | Langer et al. |

(Continued)

FOREIGN PATENT DOCUMENTS

| | | |
|---|---|---|
| DE | 3734344 A1 | 4/1989 |
| EP | 0748790 A2 | 12/1996 |

(Continued)

OTHER PUBLICATIONS

Cartolano, A. R. and Vedage, G. A., 2004, Amines by Reduction, Kirk-Othmer, Encyclopedia of Chemical Technology, John Wiley & Sons Inc; 5th edition; Jan. 31, 2004, vol. 2, pp. 478; (p. 484 and p. 485).

(Continued)

*Primary Examiner* — Clinton Brooks
(74) *Attorney, Agent, or Firm* — Donald R. Palladino

(57) ABSTRACT

The invention relates to an industrial-scale method for the vapor-phase hydrogenation of dinitrotoluene (DNT). According to said method, a stream containing DNT is sprayed into a carrier-gas stream containing hydrogen, optionally in the presence of an atomizing gas, unevaporated liquid droplets are extracted from the substantially gaseous stream that is obtained and the resultant gas stream is catalytically hydrogenated to form diaminotoluene.

7 Claims, 6 Drawing Sheets

(56) References Cited

U.S. PATENT DOCUMENTS

| | | | |
|---|---|---|---|
| 5,877,350 | A | 3/1999 | Langer et al. |
| 5,962,365 | A | 10/1999 | Langer et al. |
| 6,359,177 | B1 | 3/2002 | Brady et al. |
| 7,307,190 | B2 | 12/2007 | Pennemann et al. |
| 7,595,424 | B2 | 9/2009 | Vanoppen et al. |
| 8,110,073 | B2 | 2/2012 | Pennemann et al. |
| 9,067,864 | B2 | 6/2015 | Sommer et al. |
| 2008/0146847 | A1 | 6/2008 | Pohl et al. |
| 2011/0275858 | A1 | 11/2011 | Coelho Tsou et al. |

FOREIGN PATENT DOCUMENTS

| | | |
|---|---|---|
| GB | 599252 | 3/1948 |
| GB | 832939 | 4/1960 |
| GB | 1490313 | 11/1977 |

OTHER PUBLICATIONS

Perry's Chemical Engineers' Handbook, 8th edition, Section 19; Reactors, 2007 (pp. 19-1 to 19-61).
Perry's Chemical Engineers' Handbook, 7th edition, Section 23; Chemical Reactors, 1999 (pp. 23-1 to 23-62).
Richter, Thomas; "Zerstauben von Flussigkeiten", expert Verlag, Renningen, 2004, Chapters 3.4 (pp. 39-42), 1.3 (pp. 54-56), 4.4 (pp. 57-65), 5.7 (pp. 80-84) and 65 (pp. 101-117).
Wozniak, Gunter; "Zerstaubungstechnik"; Springer, 2003, Chapters 5.1, 5.2., 5.3, 5.4 and 5.5 (pp. 59-87).

METHOD FOR PRODUCING DIAMINOTOLUENE

CROSS-REFERENCE TO RELATED APPLICATIONS

This Application is a National Phase Application of PCT/EP2014/071125, filed Oct. 2, 2014, which claims priority to European Application No. 13187648.4, filed Oct. 8, 2013, each of which being incorporated herein by reference.

FIELD

The invention relates to an industrially implementable process for the gas-phase hydrogenation of dinitrotoluene (DNT), in which a DNT-containing stream is, optionally in the presence of an atomizing gas, sprayed into a hydrogen-containing carrier gas stream, the essentially gaseous stream obtained is freed of unvaporized liquid droplets and the resulting gas stream is catalytically hydrogenated to form toluenediamine.

BACKGROUND

Aromatic amines are important intermediates which have to be available cheaply and in large amounts. Plants having very large capacities therefore have to be built for, for example, the hydrogenation of dinitrotoluene (hereinafter also referred to as DNT). The hydrogenation product toluenediamine (hereinafter also referred to as TDA) is an important intermediate in the preparation of tolylene diisocyanate which is of great importance in polyurethane chemistry. There are numerous publications relating to the preparation of toluenediamine. By far the largest part of the prior art is concerned with the hydrogenation of dinitrotoluene in the liquid phase. Known processes include a "single-phase" process, either without further solvent (see, for example, U.S. Pat. No. 3,093,685) or using solvents which dissolve both DNT and the TDA/water mixture formed, for example simple aliphatic alcohols (e.g. methanol). In addition, there are also "two-phase" processes in which solvents (e.g. hydrocarbons) which dissolve DNT but not the TDA/water mixture formed are used, so that phase separation occurs; see, for example, GB 1 490 313. The catalyst (for example Pd/C, Raney Ni, Ni/SiO$_2$, etc.) is usually slurried in the liquid phase (therefore also referred to as "slurry-phase process"). Possible reactors are, for example, loop reactors or stirred vessels (see, for example, US 2011/295039 A1). All industrially relevant processes at present work in the liquid phase. Liquid-phase hydrogenation processes at elevated temperatures and the gas-phase hydrogenation of dinitrotoluene do not play any role industrially because of the potential hazards resulting from the thermal instability of, in particular, technical-grade dinitrotoluene. The gas-phase hydrogenation of nitroaromatics having little volatility and/or temperature sensitivity is considered to be critical in the literature (see, for example, Cartolano, A. R. and Vedage, G. A., 2004, Amines by Reduction, Kirk-Othmer, Encyclopedia of Chemical Technology, John Wiley & Sons Inc.; 5$^{th}$ edition (Jan. 31, 2004), Vol. 2, page 478 and page 484, Online-ISBN: 9780471238966).

GB 599,252 and U.S. Pat. No. 3,136,818 describe processes for preparing aromatic monoamines, in particular aniline, in the gas phase by hydrogenation in a fluidized-bed reactor. Since mononitroaromatics are substantially more stable than dinitroaromatics, uncontrolled thermal decomposition does not present a significant problem. GB 599,252 explicitly warns against the gas-phase hydrogenation of starting materials having relatively high proportions of dinitro compounds.

DE-B 1 809 711 is concerned with a process for the gas-phase hydrogenation of nitro compounds and in particular addresses the problem of uniform introduction of liquid nitro compounds into a hot gas stream by atomization, preferably at constricted places directly upstream of the reactor. The danger of possibly incomplete vaporization of the nitro compound is not mentioned. Although this document speaks in general terms of nitro compounds, it gives a specific example only for nitrobenzene. The process parameters mentioned in the document are optimized for nitrobenzene.

DE-A 3 636 984 describes a process for the coupled production of nitroaromatics and dinitroaromatics from the corresponding hydrocarbons by nitration and subsequent hydrogenation. The hydrogenation is carried out in the gas phase at temperatures of from 176 to 343.5° C. A description is given of an apparatus for the gas-phase hydrogenation which consists essentially of two reactors connected in series with intermediate cooling and intermediate introduction of starting material, but nothing is said about the size and structure of these. The problems of decomposition of dinitrotoluene is not addressed in the document.

The documents EP 0 696 573 A1, EP 0 696 574 A1, EP 0 748 789 A1, EP 0 748 790 A1 and DE 10 2006 035 203 A1 are concerned with a gas-phase process for the hydrogenation of aromatic nitro compounds which is carried out under purely adiabatic conditions. EP 0696574 A1 describes the process for preparing aromatic amines, in which a gas mixture consisting of nitroaromatics and hydrogen is passed over the catalyst under adiabatic conditions, in a quite general way. According to the other documents mentioned, particular advantages are in each case achieved in the processes by changing various parameters. The processes are applicable to nitroaromatics of the general formula

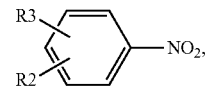

where R2 and R3 can be, inter alia, a methyl group. However, the focus of said documents is on aniline (the examples are concerned with the hydrogenation of nitrobenzene). The documents mentioned do not go into particular aspects of the hydrogenation of dinitrotoluene.

GB 832,939 is concerned specifically with the hydrogenation of dinitro compounds in the gas phase. This document discloses the use of nickel sulfide catalysts on an aluminum oxide support material. According to the document, the use of these makes an unexpectedly rapid reaction in excellent yields possible. The document does not go into process engineering details in respect of vaporization. The hydrogenation is carried out at ambient pressure and temperatures of about 220° C. (cf. examples), i.e. below the decomposition temperature of liquid pure dinitrotoluene.

DE 3734344 A1 describes the conversion of dinitrotoluene (DNT) in the gas phase into toluenediamine (TDA). DNT is vaporized in an inert, hot carrier gas within from 2 to 120 seconds to give a mixture which is composed of vaporized DNT and carrier gas and has a temperature of from 150 to 250° C. As suitable types of vaporizer, mention is made of thin film evaporators having smooth tubes, short path evaporators, falling film evaporators without circulation of liquid and single-coil helically coiled tube evaporators. The low volatility and ready decomposition of DNT and the explosion risk associated therewith are mentioned. Measures for avoiding decomposition or for avoiding accumulation of high-boiling, thermally sensitive impurities are not described since they presumably were not a problem because of the short time of the experiment of a few hours and possibly because of the purity of the starting materials used in the experiments carried out. The possible presence of nonvolatile components in the DNT is mentioned only insofar as the vaporization process can theoretically be used for separation into DNT and nonvolatile components. The hydrogenation is, according to this document, carried out in the temperature range from 200 to 450° C. and preferably at atmospheric pressure.

It is not possible to derive any technical concept for an economical reaction on a large scale from the literature sources which expressly refer to the possibility of hydrogenating DNT in the gas phase. The literature (in particular GB 832939 and DE 3734344 A1) does not address either the hurdles to be overcome in implementing an industrial DNT hydrogenation process or the utilization of the advantages potentially associated with such a process.

In respect of the industrial production of TDA by a gas-phase process, it has to be noted that DNT of technical-grade purity can have a higher proportion of relatively nonvolatile accompanying components than DNT which is used in small batches for laboratory experiments. For economic reasons, it is desirable to be able to use technical-grade DNT without complicated and expensive prepurification. This requires particular measures in the vaporization of DNT in industrial production plants.

None of the abovementioned documents gives any indication that systematic steps have been undertaken in order to allow safe vaporization and gas-phase hydrogenation of dinitrotoluene of technical-grade purity for long periods of operation and on an industrial scale, without DNT or its accompanying components decomposing in an uncontrolled manner. Little information is likewise given about
  a) critical temperature limits for avoidance of thermal decomposition of DNT,
  b) handling accompanying materials which vaporize with difficulty or not at all and have a hazard potential (e.g. picric acid, cresols, trinitrotoluene (TNT)),
  c) avoidance of the accumulation of unvaporized materials which have a hazard potential in the unvaporized state (DNT, TNT, etc.) and
  d) ensuring complete conversion of DNT before the product gas stream is cooled.

The hydrogenation of DNT liberates large quantities of energy. In the conventional liquid-phase process, hydrogen is introduced at an absolute pressure of from about 20 to 100 bar and the reactors are operated at this pressure; see, for example, US 2008/0146847 A1 (100 bar pressure and a temperature of 150° C.). Owing to the low temperature level, utilization of the energy to be removed is possible and/or economical to only a very limited extent. If the hydrogenation reaction were to be able to be carried out at a higher temperature so that higher-pressure steam were to be able to be generated, this would have great economic value. This applies particularly to integrated systems comprising a plurality of production plants in which steam obtained in one process can be utilized in other processes (for example for heating the starting materials to the reaction temperature). Recently, carrying out the liquid-phase hydrogenation without solvent at a temperature which allows the production of steam at a pressure level of 4 bar has been reported (US 2011/0275858 A1). For this purpose, the hydrogenation was carried out at a temperature of 185° C., which was possible in a safe manner under the following conditions:
  1. A reactor having an internal heat-exchange surface and an external circuit with removal of heat was used.
  2. DNT was introduced into the catalyst suspension by means of a driving nozzle below the surface of the liquid.
  3. The average DNT concentration in the reactor was limited to a value of less than 1000 ppm.
  4. The hydrogen concentration including the hydrogen in the external circuit was set to a value of greater than 1% by volume, preferably greater than 3% by volume.

Adherence to these conditions is essential to the process described, because, inter alia, nitro and nitroso compounds can decompose explosively in the presence of TDA at elevated temperatures (DE 10 2005 008 613 A1). However, the third and fourth conditions in particular can in the case of industrial production at a temperature of 185° C. or above lead to great practical problems in the design and operation of a liquid-phase process. Matching of the individual parameters to one another is difficult to realize. As will be explained in more detail below, the present invention makes it possible to maintain a temperature of 185° C. or above so that high-pressure steam can be obtained in a gas-phase process without comparable practical limitations.

In addition, gas-phase processes have a series of other advantages. Thus, separation of the catalyst from the product is easier since the product leaves the reactor in gaseous form while the catalyst remains in the reactor. Scale-up of the process is also simpler in the case of gas-phase reactors than in the case of the reactors customary in the slurry-phase process. Since mechanical stirring is not necessary in the gas-phase process, the risk of plant downtimes due to caking on the stirrer and also the energy consumption is lower. In addition, gas-phase reactors are simpler to clean than stirred vessels.

A further advantage of an industrial TDA synthesis in the gas phase arises from the possibility of subjecting the gaseous product to a prefractionation (including isomer separation) in a simple way by fractional condensation at different temperatures. Each of the condensate fractions obtained in this way can be fed in at a different place matched precisely to this fraction in the subsequent distillation sequence. This gives the possibility of considerably simplifying the distillation compared to the customary distillation of the product from a liquid-phase process (up to six columns, see, for example, U.S. Pat. No. 6,359,177 B1).

There was therefore a need to provide a process for carrying out the hydrogenation of DNT of technical-grade purity in the gas phase, which can be implemented on an industrial scale and thus make it possible to actually make use of the many advantages of a gas-phase hydrogenation, in particular the opportunity of obtaining high-pressure steam and the simplified work-up by fractional condensation, and thereby to significantly increase the energy efficiency of the process. The particular challenge was to avoid the risk of uncontrolled decomposition of DNT and its accompanying components.

SUMMARY

Taking into account what has been said above, the present invention provides a continuous process for preparing tolu enediamine by hydrogenation of dinitrotoluene in the gas phase, which comprises the steps (I) spraying of a dinitrotoluene-comprising stream (1, 11, 12) into a hydrogen-containing carrier gas stream (2, 21, 22) in a vaporization apparatus (1000, 1010, 1020), where
  a) the temperature of the dinitrotoluene-comprising stream (1, 11, 12) is from 70° C. to 150° C., preferably from 80° C. to 100° C., and the temperature of the hydrogen-containing carrier gas stream (2, 21, 22) is from 140° C. to 300° C., preferably from 180° C. to 240° C.,
  b) the absolute pressure of the dinitrotoluene-comprising stream (1, 11, 12) is from 3.0 bar to 30 bar, preferably from 4.0 bar to 20 bar, and the absolute pressure of the hydrogen-containing carrier gas stream (2, 21, 22) is from 1.0 bar to 10 bar, preferably from 3.0 bar to 6.0 bar, where the pressure of the dinitrotoluene-comprising stream (1, 11, 12) is higher than that of the hydrogen-containing carrier gas stream (2, 21, 22), preferably from 0.01 bar to 10 bar higher,
  c) the molar ratio of hydrogen to DNT is from >6.0:1 to 900:1, preferably from 60:1 to 500:1,
  so that dinitrotoluene is vaporized within from 0.010 s to 100 s, preferably within from 0.010 s to 3.0 s, with at least 95.0% by mass, preferably at least 99.5% by mass, in each case based on the total mass of all the dinitrotoluene present in the dinitrotoluene-comprising stream (1, 11, 12), being brought into the gas phase and an essentially gaseous stream (3, 31, 32) which comprises dinitrotoluene and hydrogen and may also contain proportions of unvaporized, relatively nonvolatile accompanying components of the dinitrotoluene being obtained in this way;

(II) removal or targeted decomposition, preferably removal, of the liquid droplets present in the essentially gaseous stream (3, 31, 32) comprising dinitrotoluene and hydrogen from step (I) in an apparatus (2000, 2010, 2020) so that the resulting gas stream (4, 41, 42) which comprises dinitrotoluene and hydrogen and has been depleted in liquid droplets preferably contains not more than 1000 ppm, particularly preferably not more than 500 ppm, very particularly preferably not more than 100 ppm, extraordinarily very particularly preferably not more than 50 ppm, of unvaporized droplets, based on the total mass of all the dinitrotoluene present in the dinitrotoluene-comprising stream (1, 11, 12);

(III) reaction of the dinitrotoluene present in the gas stream (4, 41, 42) which comprises dinitrotoluene and hydrogen and has been depleted in liquid droplets with hydrogen in at least one reaction space (3000, 3010, 3020) in the presence of a catalyst (100, 110, 120) at an absolute pressure of from 1.0 bar to 10 bar, preferably from 3.0 bar to 6.0 bar, a temperature of from 140° C. to 300° C., preferably from 180° C. to 270° C., and a residence time in the reaction space of from 0.1 s to 10 s, preferably from 1.0 s to 5.0 s, so as to give a toluenediamine-containing gas stream (5, 51, 52), (IV) separation of the toluenediamine-containing gas stream (5, 52) obtained in step (III) after passing through the last reaction space (3000, 3020) into a toluenediamine-comprising liquid phase (6, 6a, 6b, 6c) and a hydrogen-comprising gas phase (7) by condensation, preferably in a condensation apparatus (4000), particularly preferably by multistage condensation (4010, 4020, 4030) at a temperature which decreases from stage to stage; and (V) recirculation of at least part of the hydrogen-comprising gas phase (7) obtained in step (IV) into the first vaporization apparatus (1000, 1010) of step (I).

In this context, a vaporization apparatus is any apparatus which is suitable for spraying the DNT stream 1 (11, 12) into the carrier gas stream (the "feed hydrogen" stream) 2 (21, 22) and very completely vaporizing the DNT. In the embodiment shown in FIG. 1, solid lines, the "feed hydrogen" stream 2 is, for example, a mixture of "recycle gas hydrogen" 7 and fresh hydrogen 200; in the embodiment shown in FIG. 1 with broken lines, it is identical to the recycle gas hydrogen (7). The vaporization apparatus comprises at least one apparatus for spraying the stream 1 (11, 12) into the stream 2 (21, 22). In the simplest case, the vaporization apparatus comprises merely a pipe through which the stream 2 (21, 22) flows and into which an apparatus through which stream 1 (11, 12) is sprayed in opens. An "apparatus for spraying" is preferably a nozzle (see below for details).

The first vaporization apparatus (1000, 1010) refers, when a plurality of reaction spaces connected in series are used and thus also when a plurality of vaporization apparatuses arranged in series in the flow direction of the reaction mixture are used (cf., for example, FIG. 3), to the first vaporization apparatus in the flow direction of the reaction mixture, i.e. in the embodiment shown in FIG. 3 the vaporization apparatus 1010. In the case of a plurality of reaction spaces connected in parallel and thus also a plurality of vaporization apparatuses connected in parallel, all vaporization apparatuses arranged first in the flow direction of the reaction mixture are "first vaporization apparatuses" within the meaning of step (V). If only one reaction space and thus also only one vaporization apparatus is present (cf., for example, FIG. 1), this vaporization apparatus is naturally also "the first" vaporization apparatus within the meaning of step (V).

Here, the statements that at least 95.0% by mass, based on the total mass of all the dinitrotoluene present in the dinitrotoluene-comprising stream (1, 11, 12) are brought into the gas phase [step (I)] and the gas stream 4 (41, 42) preferably contains not more than 1000 ppm of unvaporized droplets, based on the total mass of all the dinitrotoluene present in the dinitrotoluene-comprising stream (1, 11, 12) [step (II)] in each case refer to DNT as such, i.e. without taking into account the impurities which are always present in technical-grade DNT. When stream 1 (11, 12) is, for example, a dinitrotoluene having a purity of 98% which is fed at a kg/h to the vaporization in step (I), at least 0.95·0.98·a kg/h of gaseous dinitrotoluene are fed with stream 3 (31, 32) to the droplet removal in step (II). The residual droplet content in the gas stream (4, 41, 42) which comprises dinitrotoluene and hydrogen and has been depleted in liquid droplets is preferably determined by laser-optical measurement, by means of a capacitive measurement technique or by withdrawal of a representative substream and determination of its droplet content by means of abovementioned techniques or by collection and weighing of the droplets. The above-described methods with which a person skilled in the art is familiar generally give the same results within normal error tolerances which do not detract from the reliability of the result. Should different measurement methods nevertheless give significantly different values, the result from the laser-optical measurement is decisive according to the invention.

For the purposes of the present invention, the term reaction space (step (III)) refers to the space in which DNT and hydrogen react with one another in the presence of the catalyst. The reaction space is located in an industrial apparatus for carrying out chemical reactions, viz. the reactor. In the case of a reactor which is completely filled with catalyst (for example in the form of a bed of catalyst spheres), the reaction space is identical to the interior volume of the reactor. When a plurality of reaction spaces are present, these can be connected in series or in parallel. The last reaction space refers in the case of a plurality of reaction spaces connected in series (cf., for example, FIG. 3) to the last reaction space in the flow direction of the reaction mixture, i.e. in the embodiment shown in FIG. 3 the reaction space 3020. Preference is given to only the toluenediamine-containing gas stream obtained in this reaction space being separated into a gas phase (7) and a liquid phase (6). In the case of a plurality of reaction spaces connected in parallel, all reaction spaces arranged last in the flow direction of the reaction mixture are "last reaction spaces" within the meaning of step (IV). In this case, the plurality of toluenediamine-containing gas streams obtained in this way are preferably combined before the condensation. If only one reaction space is present (cf., for example, FIG. 1), this is naturally also "the last" reaction space within the meaning of step (IV).

DETAILED DESCRIPTION

Figure 1:
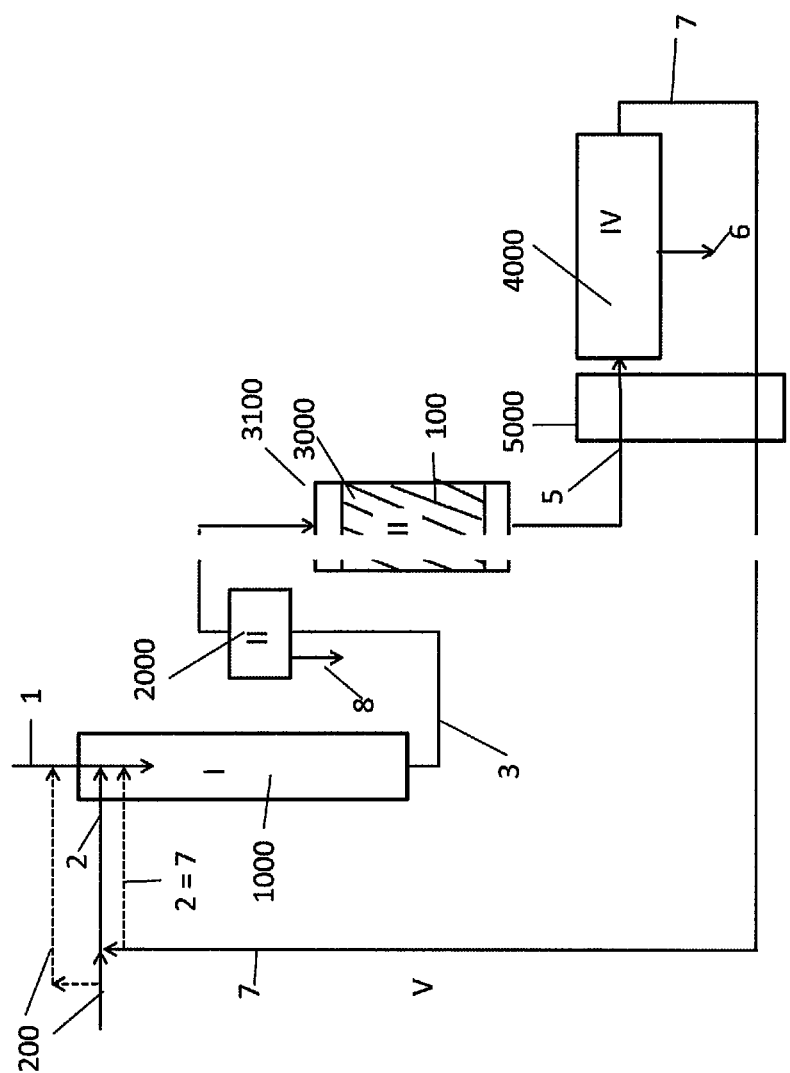
FIG. 1 illustrates a basic embodiment of the process of the present invention.

For the purposes of the present invention, residence time in the reaction space is the ratio of the volume of the reaction space through which the gas stream can flow to the volume stream exiting from the reaction space per unit time.

The invention will be described in detail below. Various embodiments are, unless the context clearly indicates the contrary, can be combined with one another as desired.

It has surprisingly been found that gaseous mixtures of vaporized DNT and a hydrogen-containing carrier gas are more thermally stable than liquid DNT or solutions of DNT having a high concentration at the same (high) temperature. This applies even in the presence of TDA with which DNT can in principle undergo undesirable reactions. A significant part of the process is therefore sufficiently complete vaporization of DNT. The process of the invention makes it possible to bring at least 99.90%, preferably at least 99.95%, particularly preferably at least 99.99%, very particularly preferably at least 99.995%, of the DNT into the gas phase (steps (I) and (II)) before it is hydrogenated in the presence of the catalyst in the reaction space to form TDA (step (III)). The maximum possible amount of unvaporized droplets of 0.10%, based on the mass of all the dinitrotoluene present in 1, is so low that no decomposition reactions to a dangerous extent have to be feared. Wherever gaseous DNT is present, i.e. in the vaporization apparatus and also in the reaction space, a temperature of 300° C. must not be exceeded; in addition, the residence time has to be kept short.

The streams 1 (DNT) and 200 (fresh hydrogen) can also contain further constituents in addition to the essential constituents DNT and hydrogen, respectively. In particular, it can be advantageous to dissolve the technical-grade DNT in a suitable solvent which is inert under the reaction conditions and is covaporized. Suitable solvents are alcohols (preferably selected from among methanol, ethanol and isopropanol). If a solvent is used, the proportion of technical-grade DNT in the solution (1) is preferably from >0% by mass to <50% by mass, based on the total mass of 1. The hydrogen, too, does not have to be used in neat form, but can be diluted with other gases which are inert under the reaction conditions of the hydrogenation. This can be effected either by the hydrogen being mixed with an inert gas before being mixed with the DNT-containing stream 1 or hydrogen and inert gas being introduced separately. Suitable inert gases are, for example, noble gases, steam, $CO_2$, nitrogen; with preference being given to nitrogen or steam. If the hydrogen is diluted with such gases before contact with the DNT-containing stream 1, the proportion thereof in the stream 2 is preferably not less than 3 mol %, based on the total molar amount of all compounds present in stream 2. For example, synthesis gas can also be used directly without the hydrogen present therein being purified to high purities. If a condensable diluent gas (e.g. steam) is used, this has the advantage that the volume stream through the compressor decreases in comparison with incondensable carrier gas.

The present process makes possible, in step (I), the vaporization of technical-grade DNT on an industrial scale. Any proportions of liquid droplets still present in the stream 3 (31, 32) are made up quite predominantly to completely of relatively nonvolatile accompanying components in the technical-grade DNT. The proportion of unvaporized droplets in stream 3 (31, 32) is therefore dependent to a substantial extent on the purity of the DNT used. The "technical-grade" DNT which is preferably used as DNT source for stream 1 (11, 12) in the process of the invention preferably comprises:
from 99.00% by mass to 99.94% by mass of DNT, with 2,4- and 2,6-DNT making up the major part (>95% of the DNT present in 1);
>5 ppm of nitrocresols;
>20 ppm of trinitrotoluene;
>500 ppm of other impurities comprising, preferably consisting of, water, mononitrotoluene, sulfuric acid and salts of sulfuric acid,
in each case based on the total amount of the technical-grade DNT 1 (11, 12).

The vaporization apparatus (1000, 1010, 1020) used has to ensure very complete vaporization of the DNT and at the same time short resonance time and minimal thermal stressing of the liquid DNT. For this purpose, apparatuses in which the DNT-containing stream 1 is sprayed into a hot hydrogen-containing carrier gas stream 2 (21, 22) by means of at least one spray apparatus (preferably a nozzle) ("spray vaporizer") are suitable for the purposes of the invention. Here, the ratio of the molar flows of 1 to 2 (21, 22) is preferably such that the proportion of DNT in 3 (31, 32) is from 0.1 mol % to 10 mol %, particularly preferably from 0.8 mol % to 2.0 mol %, in each case based on the total molar amount of all compounds present in stream 3 (31, 32). The temperature of the carrier gas stream should be selected so that as much DNT as possible can be vaporized, i.e. the DNT partial pressure is very close to the saturation pressure at the prevailing exit temperature from the vaporizer, and at the same time the maximum temperature of 300° C. allowed in the downstream reaction space at complete conversion of DNT is not exceeded. This gives a suitable temperature of the hydrogen-containing carrier gas 2 at the inlet into the vaporization apparatus of from 140° C. to 300° C., preferably from 180° C. to 240° C. To achieve very rapid (within from 0.010 s to 100 s, preferably within from 0.010 s to 3.0 seconds) and complete (at least 95.0% by mass, preferably at least 99.5% by mass, of all DNTs present in 1 (11, 12)) vaporization of the DNT, a DNT spray stream 1 (11, 12) having a very small droplet size (average droplet diameter d preferably in the range from 20 μm to 200 μm) and a uniform droplet size distribution has to be produced, as is possible with customary one-fluid and in particular two-fluid nozzles.

Suitable one-fluid nozzles are, for example, those described in Wozniak, "Zerstäubungstechnik", Springer 2003 (in particular chapters 5.1, 5.3, 5.4 and 5.5) and Richter "Zerstäuben von Flüssigkeiten", expert Verlag, Renningen, 2004 (in particular chapters 3.4, 4.3, 4.4 and 5.7). Tangential hollow cone nozzles, for example, are suitable because of the relatively small droplet diameter produced and their insensitivity to blockages. For smaller flow rates and even smaller droplet diameters, ultrasonic atomizer nozzles are suitable, also because of their variable operating range.

However, the abovementioned requirements in terms of droplet size and droplet size distribution can be satisfied most simply by means of two-fluid nozzles. In a very particularly preferred embodiment, the invention therefore provides a process in which the spraying of the stream 1 (11, 12) into the carrier gas stream 2 (21, 22) in step (I) is effected by means of at least one two-fluid nozzle (7000) through which, in addition to 1 (11, 12), a stream of an atomizing gas 9 which is under a pressure which is from 1.0 bar to 20 bar higher, preferably from 3.0 bar to 9.0 bar higher, than the absolute pressure prevailing in the surroundings on the nozzle outlet side and preferably has the same temperature as stream 2 is passed. Suitable two-fluid nozzles are described, for example, in Wozniak, "Zerstäubungstechnik", Springer 2003 (in particular chapter 5.2) and Richter "Zerstäuben von Flüssigkeiten", expert Verlag, Renningen, 2004 (in particular chapter 6.5). The mixing of 1 (11, 12) and the atomizing gas stream (9) occurs, depending on the construction of the two-fluid nozzle 7000, either in the nozzle ("internally mixing nozzle") or when the individual streams exit from the nozzle ("externally mixing nozzle"). In the first case, a two-phase mixture of 1 (11, 12) and the atomizing gas stream (9) is produced in the nozzle 7000 and is sprayed into the carrier gas stream 2 (21, 22). In the latter case, the streams containing DNT 1 (11, 12) and atomizing gas (9) are sprayed separately from one another through channels in the nozzle into the carrier gas atmosphere 2 (21, 22). Preference is given to using internally mixing two-fluid nozzles in which the streams 1 (11, 12) and 9 impinge on one another within the nozzle and leave the nozzle as a two-phase mixture.

In preferred embodiments, the invention provides a process in which steam, nitrogen, hydrogen, part of the hydrogen-comprising gas phase 7, part of the hydrogen-containing carrier gas stream (2, 21, 22) or a mixture of two or more of the abovementioned gases is used as atomizing gas 9. Very particular preference is given to using hydrogen (i.e. fresh hydrogen 200, to be distinguished from the hydrogen-containing stream 2 (21, 22), as atomizing gas 9. In the case of a plurality of reactors connected in series, stream 200 is divided (210, 220, . . . ) over the various reactors. The hydrogen consumed in the hydrogenation can in this way be replaced in a simple and advantageous manner in continuous operation with very complete recycling of the process gas 7. The mass ratio of stream 9 to stream 1 is preferably from 0.01 to 1, particularly preferably from 0.05 to 0.2. The pressure drop over the nozzle is preferably from 1.0 bar to 20 bar, particularly preferably from 3.0 bar to 9.0 bar, for stream 9 and preferably from 0.1 bar to 20 bar, particularly preferably from 3.0 bar to 9.0 bar, for stream 1.

In step (II), the already essentially gaseous stream 3 (31, 32) is freed further of liquid droplets because, inter alia, of the higher thermal sensitivity in the liquid phase. This is preferably achieved by means of one or more of the following measures:

a) separation of the remaining droplets from stream 3 (31, 32), e.g. by means of a suitable separation unit. Such a separation unit can also be installed in the reactor itself. It is then located upstream of the actual reaction space. Suitable separation units are, for example, filters, knits, deflection precipitators, cyclones and droplet precipitators known to those skilled in the art. The separation units are either dimensioned so that their function is ensured for the duration of a normal production cycle, after which they are then cleaned or regenerated in a manner known to those skilled in the art (e.g. by burning-off), or a plurality separation units are connected in parallel with one of these being in operation while the others are cleaned or regenerated.

b) targeted continuous or discontinuous decomposition of the accumulated constituents to form nonhazardous species, e.g. by suitable introduction of energy and controlled initiation of thermal decomposition.

Here, a) is preferred over b).

Since DNT and TDA can react with one another, the reaction conditions in step (III) have to be selected so that very complete conversion of the DNT is ensured within a short time. Here, the abovementioned conditions in respect of pressure, temperature and the molar ratio of hydrogen to DNT are of particular importance. Suitable catalysts are in principle the catalysts known to those skilled in the art for DNT hydrogenation, as long as they allow rapid conversion of the DNT. According to the invention, solid catalysts are used. In principle, all solid catalysts known to those skilled in the art for the hydrogenation of aromatic nitro compounds are suitable. Such catalysts are described in many publications and comprise, as hydrogenation-active elements, Pd, Pt, Ru, Fe, Co, Ni, Mn, Re, Cr, Mo, V, Pb, Ti, Sn, Dy, Zn, Cd, Ba, Cu, Ag, Au, and compounds thereof, sometimes as oxides, sulfides or selenides and also in the form of a Raney alloy, and also on inert support materials, for example $Al_2O_3$, $Fe_2O_3/Al_2O_3$, $SiO_2$, silicates, carbon, graphite, $TiO_2$, $Cr_2O_3$. Mixed oxides of the elements mentioned are likewise conceivable.

Preference is given to using a catalyst (100, 110, 120) comprising a ceramic support, preferably $Al_2O_3$, particularly preferably $\alpha$-$Al_2O_3$, very particularly preferably $\alpha$-$Al_2O_3$ having a BET surface area of less than 40 $m^2/g$, preferably less than 20 $m^2/g$, particularly preferably less than 10 $m^2/g$, and (a) from 1.0 g to 100 g, preferably from 1.0 g to 50 g, of at least one metal of groups 8 to 12 of the Periodic Table of the Elements (numbering according to IUPAC recommendation of 1986), preferably Pd, Pt, (b) from 1.0 g to 100 g, preferably from 1.0 g to 50 g, of at least one metal of groups 4 to 6 and 12 of the Periodic Table of the Elements, preferably Ti, V, Nb, Ta, Cr, Mo, W, and (c) from 1.0 g to 100 g, preferably from 1.0 g to 20 g, of at least one metal of groups 14 and 15 of the Periodic Table of the Elements, preferably Pb, Bi, per liter of bed volume of the ceramic support.

Further preferred catalysts comprise
  Pd and Rh or
  Ag and Rh
as hydrogenation-active elements, in each case on an inert support, preferably $Al_2O_3$, particularly preferably $\alpha$-$Al_2O_3$.

The reaction over a solid catalyst can be carried out largely isothermally (i.e. with removal of the heat of reaction), e.g. in a shell-and-tube reactor or fluidized-bed reactor. Suitable apparatuses are described in *Perry's Chemical Engineers' Handbook*, $8^{th}$ edition, chapter 19, 2007, and $7^{th}$ edition, chapter 23, 1999, Mcgraw-Hill Professional. It is also possible to carry out the reaction adiabatically, e.g. in a fixed-bed reactor (as described in DE 10 2006 035 203 A1, especially in paragraphs [0006], [0020] and [0030] to [0032]). In an adiabatic reactor, an adiabatic temperature increase of from 50 K to 150 K is preferably set. To maintain this temperature increase, the gas stream 4 has to be set appropriately (for example by means of a sufficiently large excess of hydrogen). A person skilled in the art will know how the required selection of the gas stream 4 can be calculated. A combination of the various modes of operation is likewise conceivable.

The removal of the heat of reaction is integrated in the reactor in the case of isothermally operated reactors (e.g. in the case of shell-and-tube reactors having a cooling circuit (e.g. oil, water or salt melt) for removing the heat of reaction). Adiabatically operated reactors are preferably followed by apparatuses for the removal of heat (e.g. heat exchangers). The temperature level allows the heat to be removed to be utilized for heating suitable heat transfer media, e.g. for generating steam having a maximum pressure, preferably from 3 to 10 bar (absolute).

Two or more reaction stages can be connected in series with or without intermediate introduction of one or more starting materials. If DNT is fed into each reactor, each reactor preferably has a dedicated DNT vaporization stage. The gas exiting from the last reaction stage is, after substantial removal of the reaction products and discharge of undesirable components, advantageously recirculated to the vaporization and/or reaction stages in order to utilize starting materials used in excess (i.e. the hydrogen), to assist vaporization and to reduce the temperature increase in the reactors.

The connection of a plurality of reaction stages in series is particularly advantageous in the case of an adiabatic reaction since the amount of DNT which can be reacted per stage can be limited firstly by the low vapor pressure and secondly by the adiabatic temperature increase. If a largely isothermal reactor is used, the use of a preceding adiabatic reaction stage, without intermediate cooling or with little intermediate cooling, can be advantageous in order to preheat the gas stream by means of the heat of reaction before vaporization, so that the vaporization of DNT is made easier. A particularly efficient embodiment of the process comprises the alternate use of adiabatic and isothermal reaction stages since the particularly high exit temperature from the adiabatic reaction stages can be utilized for vaporizing large amounts of DNT for reaction in the isothermal stages. It is also conceivable to integrate steps (I) to (III) in one apparatus.

The hydrogenation in step (III) is advantageously carried out at an absolute pressure of from 1.0 bar to 20 bar, preferably from 3.0 bar to 6.0 bar. Relatively low pressures assist DNT vaporization and heat recovery in the isolation of the product, but lead to larger dimensions of the apparatuses and a higher energy consumption for compression. In particular, the recycle stream is, on the industrial scale, limited by the maximum sizes of available apparatuses, so that a lower process pressure requires, at the same plant capacity and the same maximum recycle volume stream, more reaction stages.

Steam or nitrogen can be fed in in a targeted manner or be left in the process in the desired concentrations by means of targeted discharge in order to increase the average molar mass of the recycle gas to be compressed (averaged over all components present) in order to achieve more favorable compression in vaporization and reaction.

The reaction products toluenediamine (TDA) and water are selectively removed from the toluenediamine-containing gas stream by condensation in step (IV). In the case of a plurality of reactors connected in series, this can occur either after each reactor or preferably only after the last reactor. Suitable apparatuses for this purpose are known to those skilled in the art and are, for example, air coolers or shell-and-tube heat exchangers. Condensation preferably occurs fractionally in a plurality of condensers (4010, 4020, 4030) connected in series with a gradually decreasing condensation temperature, where the gas phase from one condenser is conveyed into the following condenser. In a preferred embodiment, condensation is carried out so that from two to five, particularly preferably four, condensate fractions are obtained. In an embodiment having five condensate fractions 6a, 6b, 6c, 6d and 6e, the condensation temperature can, for example, be decreased gradually as follows:

6a: condensation at from 175° C. to 195° C.,
6b: condensation at from 145° C. to 165° C.,
6c: condensation at from 129° C. to 149° C.,
6d: condensation at from 85° C. to 105° C.
6e: condensation at from 30° C. to 50° C.

The various condensate streams (6a, 6b, 6c, . . . ) obtained in this way are preferably introduced separately from one another at different places into a downstream distillation sequence. This distillation sequence can consist of conventional distillation columns (or an individual distillation column) with which a person skilled in the art will be familiar. In particularly preferred embodiments, the distillation sequence comprises 1. heat-integrated configurations such as columns having heat pumps or HIDICs ("heat integrated distillation columns") or
2. thermally coupled columns such as columns having side stream stripping or rectification columns, side stream vaporizers or preseparation columns or pre-vaporizers, for example Petlyuk or Kaibel configurations, or dividing wall columns.

In addition, the distillation columns can have a number of pump liquid circuits.

If a plurality of condensate fractions 6a, 6b, etc., are fed to the same distillation column, preference is given to the fractions obtained at higher temperature being introduced into the distillation column above the fractions obtained at lower temperature.

The abovementioned distillation sequences are considerably cheaper to install and to operate than a TDA distillation sequence according to the prior art having up to six distillation columns.

A substream is preferably discharged from the remaining incondensable gas stream in order to avoid accumulation of volatile undesirable components in the process. Subsequently, the pressure is preferably increased and the compressed stream is recirculated to the process (hydrogen-containing gas stream 7).

Figure 3:
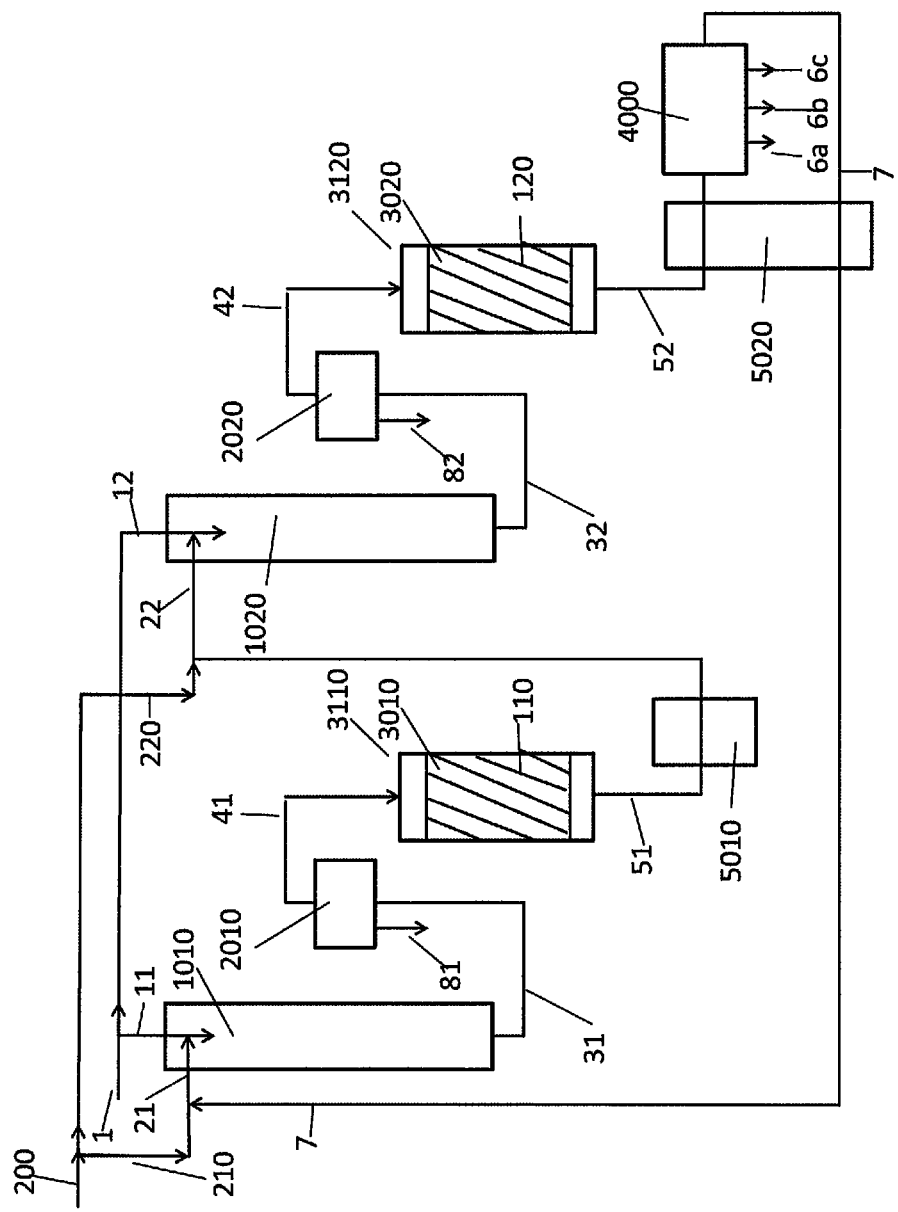
FIG. 3 illustrates an arrangement in which two adiabatically operated reactors having two vaporization apparatuses are connected in series according to some embodiments, of the present invention.

The hydrogen-comprising gas phase 7 obtained in step (IV) is recirculated in step (V) to the first vaporization apparatus (1000, 1010). In a preferred embodiment, the hydrogen-comprising gas phase 7 is used to provide the hydrogen-containing carrier gas stream 2. This can be effected by mixing fresh hydrogen 200 with the DNT-containing stream 1 (preferably in a two-fluid nozzle) before the resulting mixed stream is sprayed into the carrier gas stream 2 (in this embodiment identical to the recycled gas stream 7) (shown by broken lines in FIG. 1). As an alternative, it is also conceivable (as shown by solid lines in FIG. 1) to combine fresh hydrogen (200) with the recycled process gas stream 7 to form the carrier gas stream 2 before the DNT-containing gas stream 1 is sprayed in. In the case of a plurality of reactors connected in series, the stream 7 is used directly only for providing the carrier gas stream 2 for the first reactor. The carrier gas stream for the subsequent reactors is the toluenediamine-containing gas stream (51) or, if this is, as is preferred, enriched with fresh hydrogen (200), as shown in FIG. 3, the stream 22 which naturally contains the constituents of the stream 7.

The liquid phase 6 (or the liquid phases 6a, 6b, 6c, etc.) obtained in step (IV) contains, apart from the target product toluenediamine, mainly water and minor amounts of secondary components. Stream 6 (or the liquid phases 6a, 6b, 6c, etc.) is preferably worked up by methods known per se comprising distillation of the crude TDA in a further step (VI) in order to obtain pure toluenediamine. Suitable methods are described, for example, in U.S. Pat. No. 6,359,177 and U.S. Pat. No. 7,307,190. This work-up can be simplified significantly by a suitable prefractionation in step (IV).

Various embodiments of the invention are illustrated below with the aid of the drawings:

FIG. 1 shows, in greatly simplified form, a basic embodiment of the process of the invention having only one reactor 3100. Details such as compressors have not been shown for reasons of clarity.

Technical-grade DNT (1) is brought into the gas phase in a vaporization apparatus 1000 by spraying into the hydrogen-containing carrier gas stream 2 (step (I), solid lines). It is also conceivable to use the process gas stream 7 as hydrogen-containing carrier gas stream 2 and mix fresh hydrogen 200 with the DNT stream 1 (broken lines) before entry into the vaporization apparatus. Before entry into the reactor, the stream 3 is freed of last liquid droplets in an apparatus 2000 (step (II)). The liquid stream 8 obtained in this way is, to avoid undesirable reactions, either cooled further quickly or subjected to controlled decomposition (e.g. by irradiation with microwaves or controlled thermal decomposition brought about in another way; not shown in the figure). The gas stream 4 is introduced into the reactor 3100. In the reaction space 3000, the hydrogenation takes place in the presence of the catalyst 100 (step (III)). The gaseous product stream 5 leaving the reactor is cooled in the heat exchanger 5000 by heat exchange with stream 7 and condensed in the condensation apparatus 4000, giving a toluenediamine-comprising liquid phase 6 and a hydrogen-comprising gas phase 7. Stream 7 is, optionally after discharge of a small proportion (not shown in the figure) in order to prevent accumulation of undesirable gases, mixed with the fresh hydrogen 200 in order to obtain the hydrogen-containing carrier gas stream 2. Stream 7 is preheated in the heat exchanger 5000 by heat exchange with stream 5. Partial condensation of the stream 5 can occur already in the heat exchanger 5000. However, this will generally not be sufficiently complete, so that a condenser 4000 is installed downstream.

Figure 1A:
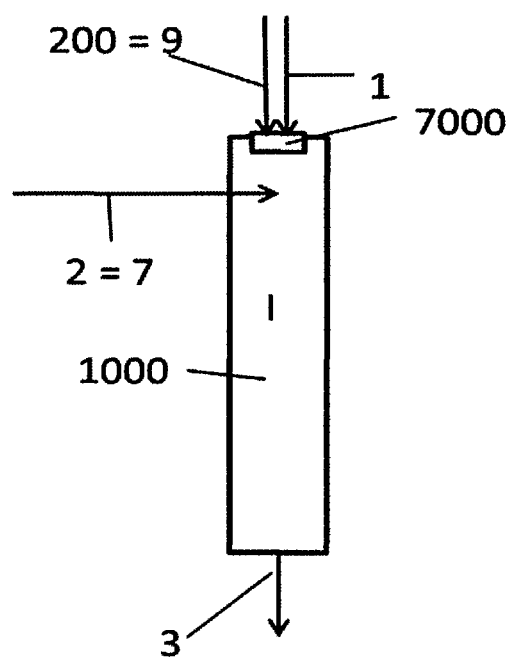
FIG. 1a illustrates, in a section of the total process of the embodiment shown in broken lines in FIG. 1, a variant of the embodiment of FIG. 1 in which a two-fluid nozzle is used.
Figure 1B:
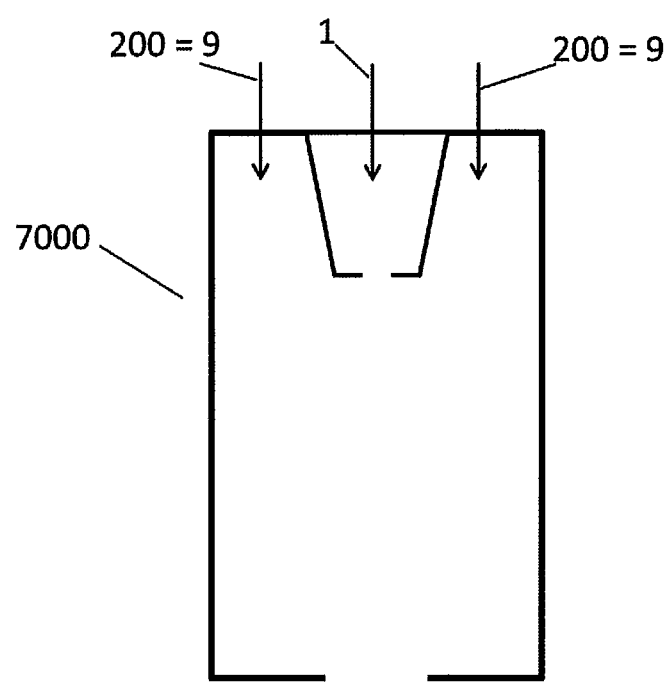
FIG. 1b illustrates a possible configuration of a two-fluid nozzle according to some embodiments of the present invention.

FIG. 1a shows, in a section of the total process of the embodiment shown in broken lines in FIG. 1, a preferred variant of this embodiment in which a two-fluid nozzle 7000 is used. Fresh hydrogen 200 serves simultaneously as atomizing gas 9. The two-fluid nozzle opens directly into the vaporization apparatus 1000. A possible configuration of a two-fluid nozzle 7000 as internally mixing nozzle is shown in FIG. 1b.

Figure 2:
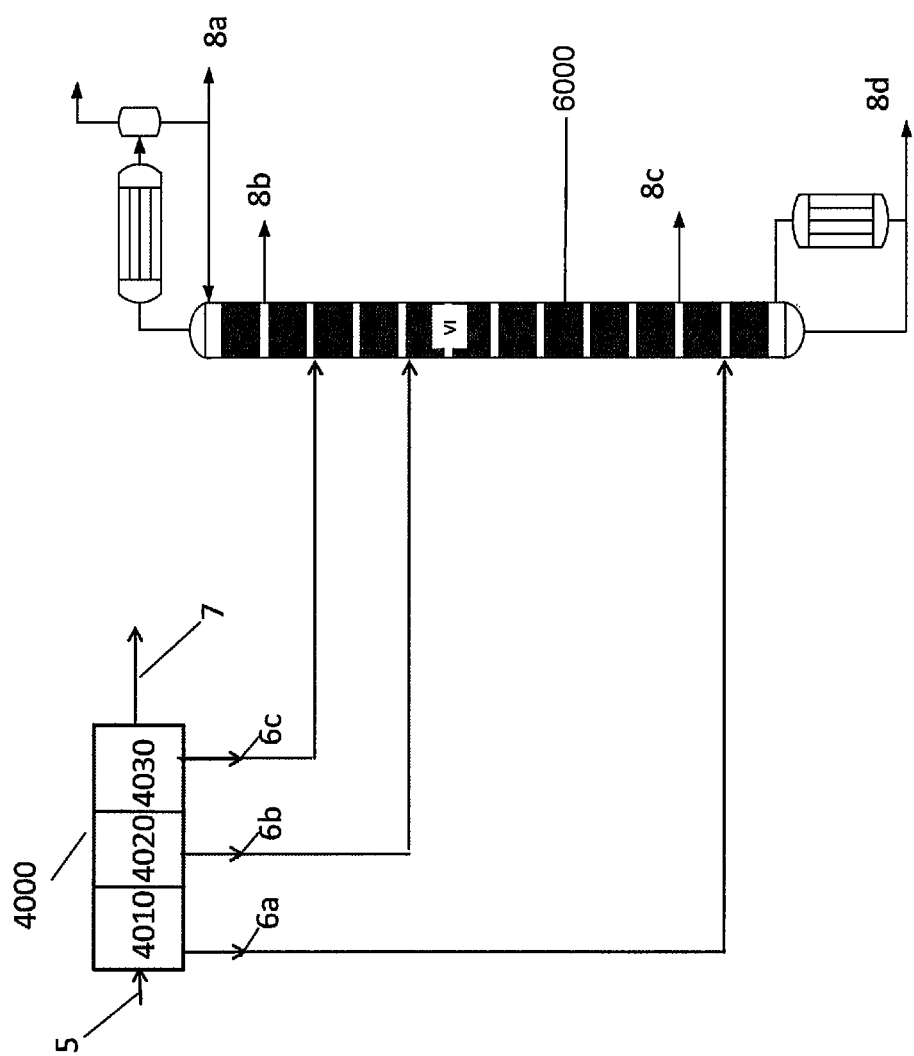
FIG. 2 illustrates a non-limiting example of a system for condensation and subsequent work-up of a gaseous product stream according to the present invention.

The condensation in the apparatus 4000 is preferably carried out in such a way that a preseparation of the crude TDA takes place at this early stage, which considerably assists the subsequent work-up (FIG. 2). For this purpose, the product 5 which is obtained in gaseous form is separated into a plurality of condensate fractions 6a, 6b, 6c, etc., by means of a fractional condensation in condensers (4010, 4020, 4030) connected in series with gradually decreasing temperature. The embodiment with three condensate streams as shown in the drawing is merely by way of example. Each of the resulting condensate fractions is fed to a different place matched precisely to this fraction in the distillation column 6000 in the subsequent distillation sequence (step (VI)). In this way, various toluenediamine fractions 8a, 8b, 8c and 8d which differ in terms of their isomer composition and secondary component content are obtained.

FIG. 3 shows an arrangement in which two adiabatically operated reactors 3110 and 3120 having two vaporization apparatuses 1010 and 1020 are connected in series instead of one reactor 3100. The depiction of two reactors is purely by way of example; the actual number of the reactors to be selected depends on many factors such as the desired production capacity, the recycle gas volume, etc. Preference is given to from 8 to 12 reactors being connected in series. The reaction route shown in FIG. 1 by broken lines can naturally likewise be used here and has not been drawn in merely for reasons of clarity.

Technical-grade DNT (1) is brought into the gas phase in a vaporization apparatus 1010 or 1020 by spraying into the hydrogen-containing carrier gas stream 21 or 22 (step (I)). Before entry into the respective reactor, the stream 31 or 32 is additionally freed of liquid droplets in an apparatus 2010 or 2020 (step (II)) so as to obtain a gas stream 41 or 42. The hydrogenation takes place under adiabatic conditions in the reactors 3110 and 3120 (step (III)). The heat of reaction is reflected, except for small unavoidable heat losses, quantitatively in a temperature increase of the gas stream (adiabatic temperature increase). The gaseous product stream 51 leaving the first reactor is cooled to the entry temperature in the following stage with generation of steam in a downstream heat exchanger 5010. After passing through the last heat exchanger 5020, the product passes through a multistage condensation and phase separation in 4000 (step IV). The streams 6a, 6b and 6c obtained here are worked up in step (VI) (not shown in the figure) to give pure TDA. The gas phase obtained is, after heat exchange with stream 52 and optionally after discharge of a small part as purge stream (not shown in the figure), recirculated as stream 7 to the process (step (V)).

The process of the invention can be carried out in various embodiments. The reaction in the reaction space 3000 (3010, 3020) can, as mentioned above, be carried out adiabatically or isothermally. The catalyst 100 (110, 120) can be present in the form of a fixed bed or a fluidized bed. The process can also be carried out in a plurality of stages (i.e. in a plurality of reaction spaces 3010, 3020, . . . ) with multiple addition of fresh DNT, with from two to 10 stages being preferred. Here, the type of reaction space 3000 can vary from stage to stage. For example, an embodiment in which adiabatically and isothermally operated reaction spaces alternate (3010: adiabatic, 3020: isothermal, 3030: adiabatic, etc.) is conceivable. Fixed-bed reactors and fluidized-bed reactors can also be combined with one another in a production plant, for example in an alternating fashion.

In addition, apparatuses for removal of heat (heat exchangers) can be provided between the individual stages. Such apparatuses for removal of heat are preferably installed downstream of the adiabatically operated reaction spaces. In the case of isothermally operated reaction spaces, the removal of heat occurs in the reaction space itself. It is likewise possible for part or all of the heat of reaction from the preceding stage to be used for the (naturally endothermic) vaporization of fresh DNT in each stage and thus to be made directly useful.

EXAMPLES

Example 1

Figure 4:
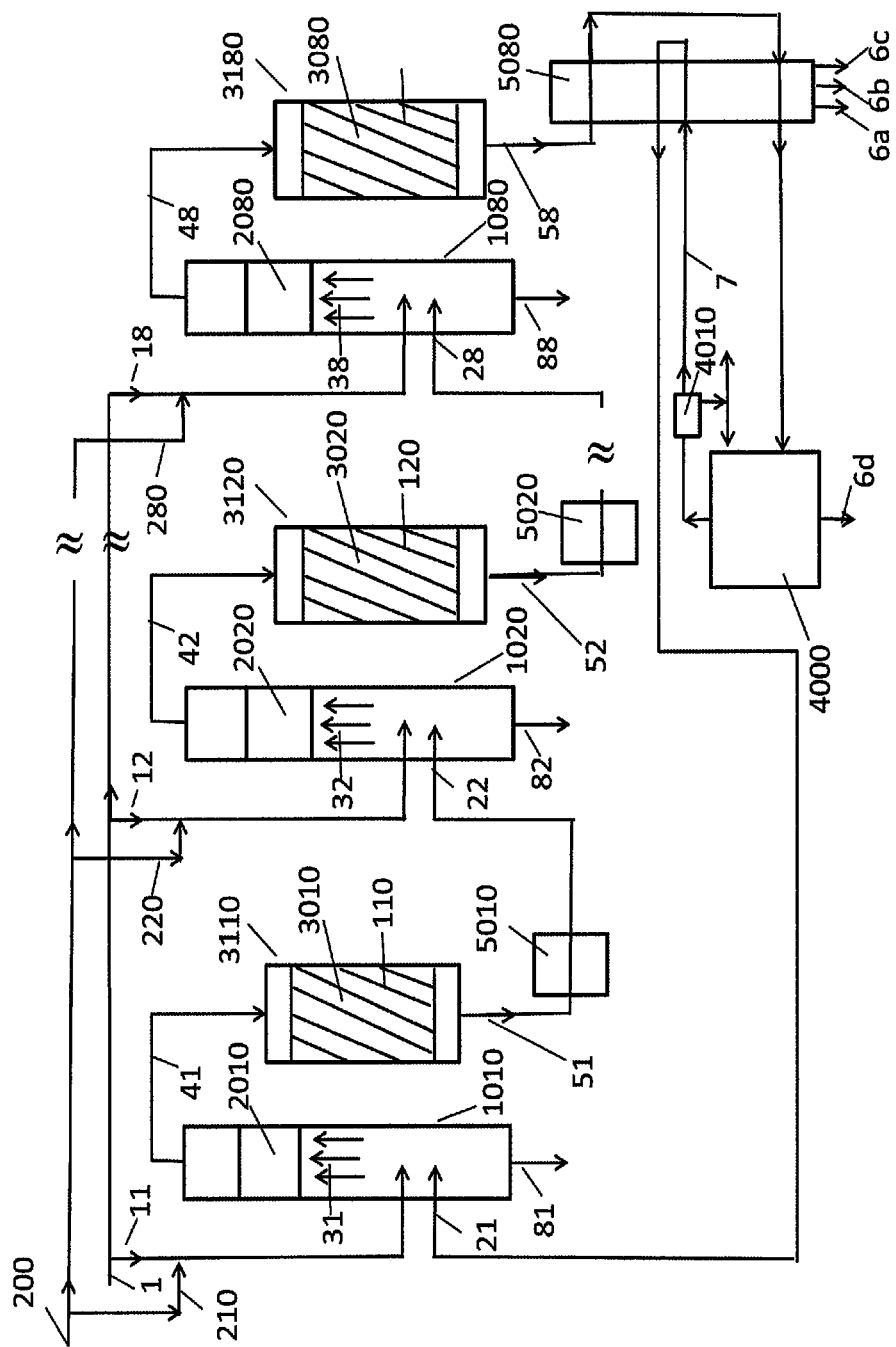
FIG. 4 illustrates a process of the present invention described in Example 1.

Process Simulation by Means of Aspen Plus® for a Process Having Eight Reactors Connected in Series; FIG. 4

39.8 metric tons of DNT (1) per hour were melted at from 70° C. to 100° C., compressed to an absolute pressure of from 10 to 20 bar and divided into eight streams (11, 12, . . . , 18). 2959 kg/h of fresh hydrogen (200) were supplied at the same absolute pressure and likewise divided into eight streams (210, 220, . . . , 280). DNT streams (11, 12, . . . , 18) and fresh hydrogen streams (210, 220, . . . , 280) were mixed with one another in two-fluid nozzles (not shown) in each case. The resulting mixed streams were fed to spray vaporizers (1010, 1020, . . . , 1080). In the first spray vaporizer, recycle gas (7; about 100 000 m³/h) under an absolute pressure of 4.2 bar was used as carrier gas stream (21) into which the DNT/fresh hydrogen mixture (11+210) was sprayed. The resulting predominantly gaseous mixed stream (31) was conveyed through a droplet precipitator (2010). The residence time of the DNT between entry into the spray vaporizer and entry into the droplet precipitator was 0.25-0.35 second. In the embodiment shown, the apparatus for droplet precipitation is integrated into the vaporization apparatus. Nonvaporizable components were taken off as liquid stream (81) at the bottom of the spray vaporizer (1010). All resulting liquid streams of unvaporizable components (81, 82, . . . , 88) were quickly cooled to a temperature below 40° C. and safely disposed of (not shown in the figure). The gas stream (41) from the spray vaporizer was fed into the reactor 3110. In the reaction space 3010, DNT was converted into TDA under adiabatic conditions. The TDA-containing recycle gas stream (51) leaving the reactor was cooled to a temperature of 180° C. in a heat exchanger (5010) with generation of 6 bar steam and fed as carrier gas stream (22) for the DNT/fresh hydrogen mixture (12+220) to the next spray vaporizer (1020). The mixed stream (32) obtained is freed of droplets as described above and converted into TDA in the reactor 3120. The further reaction in the reactors 3130 to 3180 was carried out analogously with slightly different temperatures.

The product gas stream (58) obtained after passage through the last reactor (3180) was passed through a plurality of heat exchangers (shown in simplified form as 5080) in which a fractional partial condensation to give liquid TDA-containing streams (6a, 6b, 6c) already occurred. The gas stream which remained was partially liquefied in a scrubber (4000) to give the TDA-containing liquid phase 6d. The overhead product from the scrubber (4000) was passed through a condenser (4010), the liquid phase obtained there, which consisted predominantly of water and minor proportions of low-boiling by-products and traces of TDA, partly recirculated to the scrubber and partly discharged. A small purge stream was taken off from the recycle gas stream (7) leaving the condenser (4010) and the remaining recycle gas stream (7) was compressed (both not shown in the figure). After heating by indirect heat exchange with the hot TDA gas stream 58 in 5080, the recycle gas stream (7) was fed as carrier gas stream (21=7) to the vaporization of the DNT/fresh hydrogen mixture (11+210) in the spray vaporizer (1010).

The condensation of the individual TDA fractions occurred at the following temperatures:
6a: 185° C.
6b: 155° C.
6c: 135° C.
6d: 95° C.

These four streams were fed separately from one another into a distillation column having a convection vaporizer, side offtake and overhead condenser (not shown in FIG. 4), with the stream 6a being fed into the column 5 theoretical plates above the bottom. Stream 6b was fed in above 6a, stream 6c was fed in above 6b and stream 6d was fed in above 6c. The absolute pressure at the top of the distillation column was 60 mbar. Four product streams were taken off:
gaseous overhead product comprising predominantly water and low boilers;
liquid overhead product comprising predominantly o-TDA;
a product which was taken off as side stream and comprised predominantly m-TDA (25 metric tons per hour);
bottom product comprising predominantly high boilers.
The energy consumption of the convection vaporizer was 5.5 MW at 202° C.

For such a distillation performance, the use of a plurality of distillation columns is required according to the prior art. This is made clear in the specialist literature; see, for example, Kirk-Othmer, Encyclopedia of Chemical Technology, John Wiley & Sons Inc.; 5th edition (Jan. 31, 2004), Vol. 2, page 485, online ISBN: 9780471238966, where the use of three distillation columns for removal of water and isomer separation is described. EP 1935871 A2 states that, by means of a suitable energy saving connection with the reaction section, a calculated 10.9 MW of steam from outside is required for water removal in order to obtain 25 t/h of m-TDA product stream. According to U.S. Pat. No. 7,307, 190 B2, the subsequent isomer separation can be brought about in an energy-saving manner in a dividing wall column, for which a prevaporizer power of a calculated 5.6 MW is required for obtaining 25 t/h of m-TDA product stream. According to the prior art, a total of at least 16.5 MW of vaporizer power is accordingly required in at least two columns for the fractionation of the total reaction mixture, compared to 5.5 MW in the process of the invention. In addition, the distillation according to the invention in one column is cheaper in terms of apparatus and simpler to operate than the two-column distillation sequence according to the prior art consisting of a column with heat integration of the reaction section and also a dividing wall column.

The invention claimed is:

1. A continuous process for preparing toluenediamine by hydrogenation of dinitrotoluene in the gas phase, comprising:
- (I) spraying a dinitrotoluene-comprising stream into a hydrogen-containing carrier gas stream in a vaporization apparatus, where
  - a) the temperature of the dinitrotoluene-comprising stream is from 70° C. to 150° C. and the temperature of the hydrogen-containing carrier gas stream is from 140° C. to 300° C.,
  - b) the absolute pressure of the dinitrotoluene-comprising stream is from 3.0 bar to 30 bar and the absolute pressure of the hydrogen-containing carrier gas stream is from 1.0 bar to 10 bar, where the pressure of the dinitrotoluene-comprising stream is higher than that of the hydrogen-containing carrier gas stream, and
  - c) the molar ratio of hydrogen to dinitrotoluene is from 6.0:1 to 900:1,
  - so as to give a stream comprising dinitrotoluene and hydrogen;
- (II) removing or targetedly decomposing the liquid droplets present in the stream comprising dinitrotoluene and hydrogen from step (I) to give a gas stream which comprises dinitrotoluene and hydrogen and has been depleted in liquid droplets;
- (III) reacting the dinitrotoluene present in the gas stream which comprises dinitrotoluene and hydrogen and has been depleted in liquid droplets with hydrogen in at least one reaction space in the presence of a catalyst at an absolute pressure of from 1.0 bar to 10 bar, a temperature of from 140° C. to 300° C. and a residence time in the reaction space of from 0.1 s to 10 s, so as to give a toluenediamine-containing gas stream,
- (IV) separating the toluenediamine-containing gas stream obtained in step (III) after passing through the last reaction space into a toluenediamine-comprising liquid phase and a hydrogen-comprising gas phase by condensation; and
- (V) recirculating at least part of the hydrogen-comprising gas phase obtained in step (IV) into the first vaporization apparatus of step (I).

2. The process of claim 1, wherein the spraying of the dinitrotoluene-comprising stream into the hydrogen-containing carrier gas stream in step (I) is carried out by means of at least one two-fluid nozzle through which a stream of an atomizing gas which is under a pressure of from 1.0 bar to 20 bar higher than the absolute pressure prevailing in the surroundings on the nozzle exit side is passed in addition to the dinitrotoluene-comprising stream.

3. The process of claim 2, wherein steam, nitrogen, fresh hydrogen, part of the hydrogen-comprising gas phase, part of the hydrogen-containing carrier gas stream or a mixture of two or more of the abovementioned gases is used as atomizing gas.

4. The process of claim 1, wherein the condensation in step (IV) is carried out fractionally with a gradually decreasing condensation temperature so that a plurality of toluenediamine-comprising liquid phases are obtained.

5. The process of claim 1, further comprising:
- (VI) working UP the toluenediamine-comprising liquid phase and/or the toluenediamine-comprising liquid phases obtained in step (IV) by distillation in order to obtain pure toluenediamine.

6. The process of claim 5, wherein the condensation in step (IV) is carried out fractionally with a gradually decreasing condensation temperature so as to give a plurality of toluenediamine-comprising liquid phases which are, in step (VI), introduced separately from one another into various places in the work-up by distillation.

7. The process of claim 1, wherein the dinitrotoluene in the dinitrotoluene-comprising stream has the following composition:
- from 99.00% by mass to 99.94% by mass of dinitrotoluene,
- >5 ppm of nitrocresols,
- >20 ppm of trinitrotoluene, and
- >500 ppm of other impurities comprising water, mononitriotoluene, sulfuric acid and salts of sulfuric acid,
- in each case based on the total mass of the dinitrotoluene in the dinitrotoluene-comprising stream.

* * * * *